United States Patent [19]
Traut et al.

[11] Patent Number: 5,795,315
[45] Date of Patent: Aug. 18, 1998

[54] MULTIPLE-SIZE CERVICAL COLLAR

[75] Inventors: James R. Traut; Sean L. Phillips, both of Poughkeepsie, N.Y.; Gordon D. Row, Lexington, Mass.

[73] Assignee: Laerdal Medical Corporation, Wappinger Falls, N.Y.

[21] Appl. No.: 780,024

[22] Filed: Dec. 23, 1996

[51] Int. Cl.⁶ ........................................................ A61F 5/00
[52] U.S. Cl. ........................................ 602/18; 128/DIG. 23
[58] Field of Search ........................ 602/17–19; 128/97.1, 128/870, DIG. 23

[56] References Cited

U.S. PATENT DOCUMENTS

| | | | |
|---|---|---|---|
| 5,267,951 | 12/1993 | Ishii | 602/26 |
| 5,433,696 | 7/1995 | Osti | 602/18 |
| 5,437,612 | 8/1995 | Moore et al. | 602/18 |

*Primary Examiner*—Linda C. Dvorak
*Attorney, Agent, or Firm*—Kenyon & Kenyon

[57] ABSTRACT

A multiple-size cervical collar is disclosed which is formed from a stiff flexible plastic material and comprises (a) a neck encircling band comprising a front portion and a back portion and (b) a mandible support formed from such plastic material. The mandible support is vertically shiftable with respect to the neck band and lockable thereto at a discrete number of positions to match standard single-sized collars and thereby accommodate various sizes of wearers to which the collar is applied.

40 Claims, 11 Drawing Sheets

MULTIPLE-SIZE CERVICAL COLLAR

FIELD OF THE INVENTION

The present invention relates generally to cervical collars, and more particularly to cervical collars that are suitable for multiple sizes of use.

BACKGROUND OF THE INVENTION

Cervical collars have been used by physicians and emergency medical technicians for a number of years. Such devices provide initial support of the head in a neutral position. The fundamental task of any cervical collar is to geometrically constrain the wearer's head relative to his neck and back to minimize further (and possibly damaging) movement. In order to meet this goal, the collar must be sized so as to accommodate the geometrical parameters presented by the wearer, such as the circumference of his neck and his neck length—the distance between the wearer's mandible and the top of the wearer's shoulder (at the trapezius muscle). If the collar is not properly fitted to the wearer, the wearer's head may not be supported in a neutral position with the proper degree of support against unwanted movement.

Variations of neck circumference can be dealt with in an economical manner by various strapping systems now on the market, such as that set forth in U.S. Reissue Pat. No. 32,219 to Garth. More problematic is accommodating the differences in neck lengths, that is, the range of mandible-shoulder distances that are typically encountered. One solution to this problem is to provide collars of various sizes. Many manufacturers use this technique. It is common for a manufacturer to produce four different sizes to accommodate the differences among adults. Unfortunately, stocking multiple sizes of collars can be unwieldy, and adds to inventory costs. In an emergency response environment such as in an ambulance, space is at a premium and stocking multiple sizes requires additional space, which is difficult to accommodate. Even where such space is available, the inexperienced technician may inadvertently select the wrong size of collar, or simply may not have the correct size of collar on hand, and attempt to fit a collar of the wrong size to the wearer with harmful effect.

There is, therefore, a need for a single cervical collar that can accommodate a variety of wearer sizes, including variation in neck length, so as to minimize the storage and transport space requirements. To further minimize storage space required of such a collar, it would ideally be generally flat (and stackable) in its stored state.

It is known to provide a collar that has a height-adjustable feature, and such is shown in a collar manufactured by the Sure-Loc company under the trade-name Sure-Loc. Unfortunately, this collar does not provide adequate support of both the mandible and mastoid process across its adjustment range, with the result that it permits lateral and rotational motions of the head. There is a need for a cervical collar that in addition to offering multiple sizes in a single collar, provides adequate support to the mandible and the mastoid process across its range of sizes, thereby preventing lateral bending and rotation, in addition to flexion/extension movements of the head.

Another desirable feature of a multi-size collar is that it be easy to use and can be speedily fitted to a wearer. Collars are known that provide variable positioning essentially anywhere between upper and lower limits, but these are often not easy to use. For example, U.S. Pat. No. 2,911,970 to Bartels discloses a collar in which the height is set by tightening screws at any arbitrary point between upper and lower bounds. This collar requires the use of a tool (a screwdriver) to properly fit the collar, which is a drawback in many settings.

A further requirement of a cervical collar is that it can be speedily fitted to a wearer in a risk-free manner. As a practical matter, this suggests a collar that can be sized to a wearer entirely before being fitted to him. Given the chaotic circumstances under which collars must be fitted to wearers in emergency situations, this is of great importance. U.S. Pat. No. 5,520,619 to Martin discloses an adjustable cervical collar in which a complex system of ratchet and pawls provide for highly selective degree of adjustment virtually anywhere within an adjustment range. The collar is fitted to the wearer and adjusted while it is on the wearer by moving the ratchet and pawls relative to one another until the sternum and shoulder brace described therein is set in place against the wearer's sternum. The adjustment of a collar while it is attached to a wearer is potentially harmful to the wearer, as it may occasion further undesirable movement of his head relative to his shoulder. Moreover, the possibility exists that the technician fitting the collar will position it so that it is excessively tight, resulting in additional wearer discomfort that can only be corrected by pulling at the adjustment structure while the collar is attached to the wearer. There remains a need for a collar which can be sized entirely apart from the wearer, and preferably can be readily positioned in one of the standard collar sizes that have won general acceptance in the field.

Cervical collars also must be compatible with other devices that are often used with them, such as extrication devices, backboards, straps, padding, etc., and should not present any hindrances to airway management (which involves the use of face masks, establishment of oral airways, and endotracheal intubation) or access to the throat or spine (establishing surgical airways, palpating the pulse at the carotid arteries, assessing spinal trauma etc.) One of the disadvantages of the aforementioned Sure-Loc collar is that its vertical adjustment mechanism obstructs access to the throat of the wearer. There is a need for a collar which can assume multiple sizes that does not so limit access to the throat of the wearer.

Ease and cost of manufacture are additional and increasingly important considerations, particularly as changes to the economic basis of health care give rise to increasing pressure for lower cost products. Many collars on the market call upon a multiplicity of parts. An example of such a collar is the aforementioned collar described in U.S. Pat. No. 5,520,619 to Martin, which utilizes a variety of separately manufactured parts (such as pawls and rows of ratchet teeth) that increase the manufacturing cost of the article. There remains a need for a cervical collar in which accommodating various sizes does not compromise economy.

Finally, the collar should also be comfortable to the wearer, both for physical and psychological reasons.

SUMMARY AND OBJECTS OF THE INVENTION

It is an object of this invention to provide a cervical collar that constrains the head of a wearer against lateral, rotational, flexion and extension motions.

It is an object of this invention to provide a cervical collar that provides mandibular support.

It is an object of this invention to provide a cervical collar that provides a high degree of access to the neck of the wearer.

It is an object of this invention to provide a cervical collar that can be sized to any one of the standard collar sizes prior to being attached to the wearer.

It is an object of this invention to provide a cervical collar that requires little storage space.

It is an object of this invention to provide a cervical collar that is economical to manufacture.

These objects are met with a cervical collar that is formed from a stiff flexible plastic material and which comprises: (a) a neck encircling band comprising a back portion and a front portion; and (b) a mandible and chin support, also formed from stiff flexible material. The mandible support is connected to the front portion of the neck band via a series of slots and sliders that permits shifting (i.e., altering height, or vertical adjustment) of the mandible support with respect to the neck band. A series of holes in the mandible support cooperates with tabs on the neck band to lock the configuration of the collar into one of a discrete number of vertical positions corresponding to a preselected collar size. Padding is provided on both the neck band and mandible support for wearer comfort.

The cervical collar is secured to the wearer with straps comprising hook and loop type fasteners attached to the ends of the neck band. The hook portion of the fastener may be molded directly onto the plastic of the neck band to simplify assembly of the cervical collar.

BRIEF DESCRIPTION OF THE FIGURES

For a more complete understanding of this invention, reference should now be made to the embodiments illustrated in greater detail in the accompanying drawings and described below. In the drawings.

DETAILED DESCRIPTION

Figure 1:
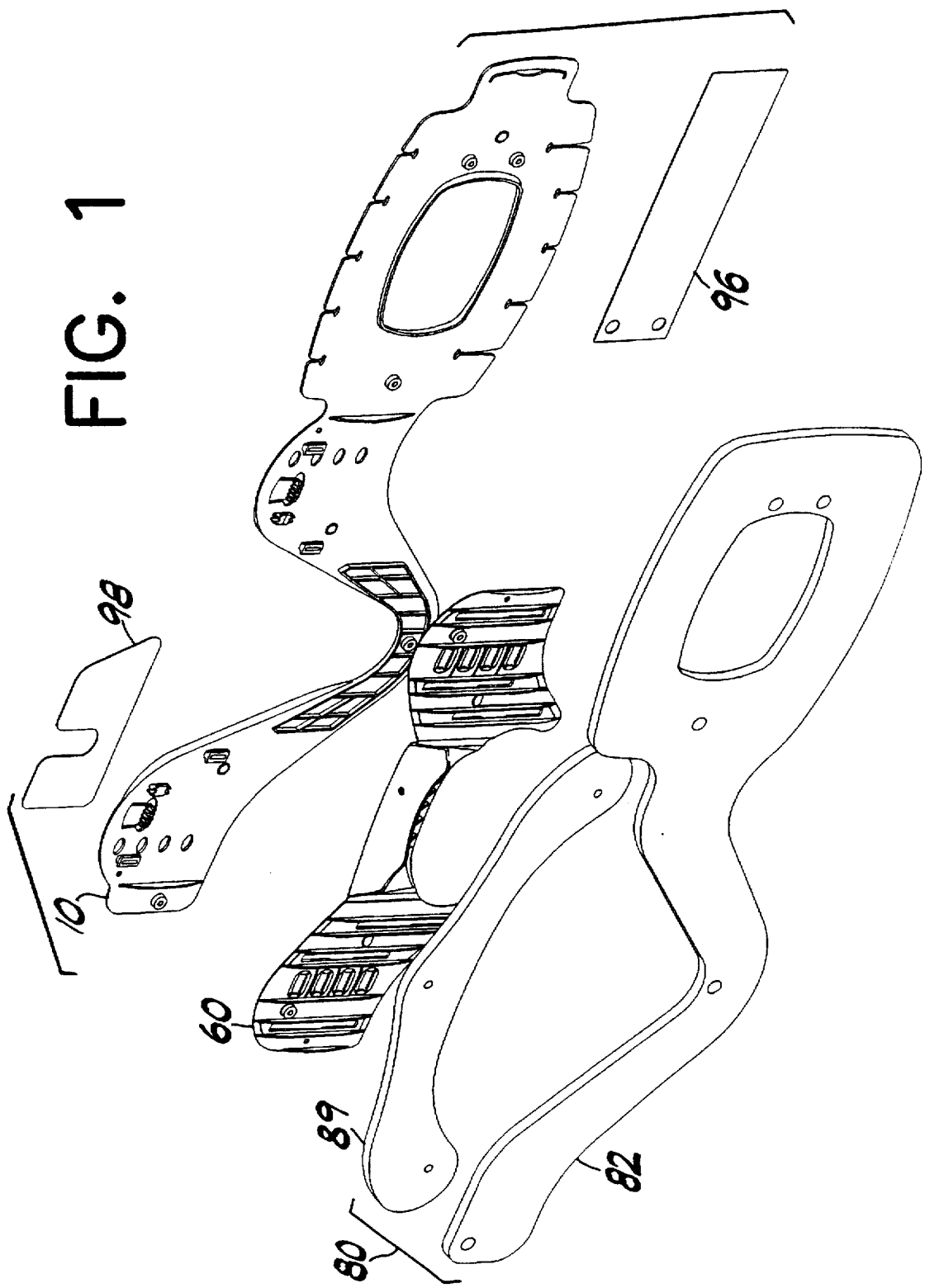
FIG. 1 is a perspective, exploded view of a first embodiment of a multi-size or position cervical collar constructed according to the principles of the invention, as viewed from the interior side of the collar.
Figure 2:
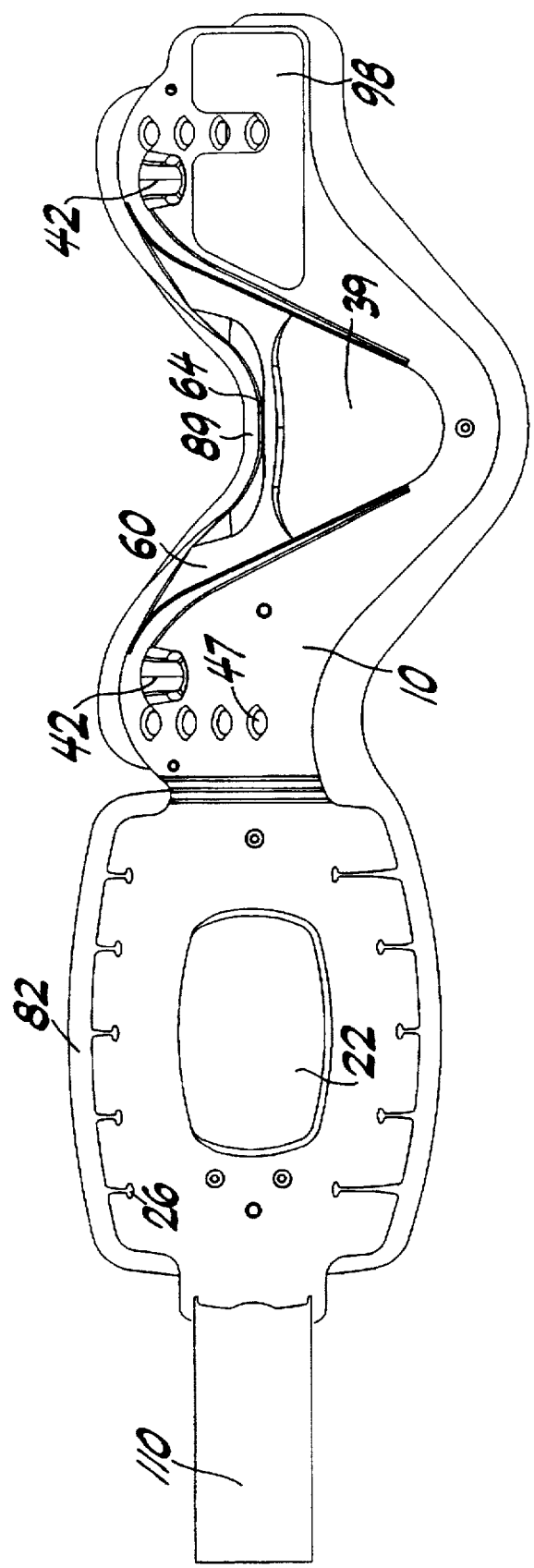
FIG. 2 is a plan view of the exterior side of the collar shown in FIG. 1.

Referring now to the drawings, wherein like numerals indicate like parts throughout, the principal components of a preferred embodiment of a multiple size cervical collar are illustrated in FIG. 1. The collar comprises a neck band 10, a mandible support 60, foam padding, and strapping.

Figure 3:
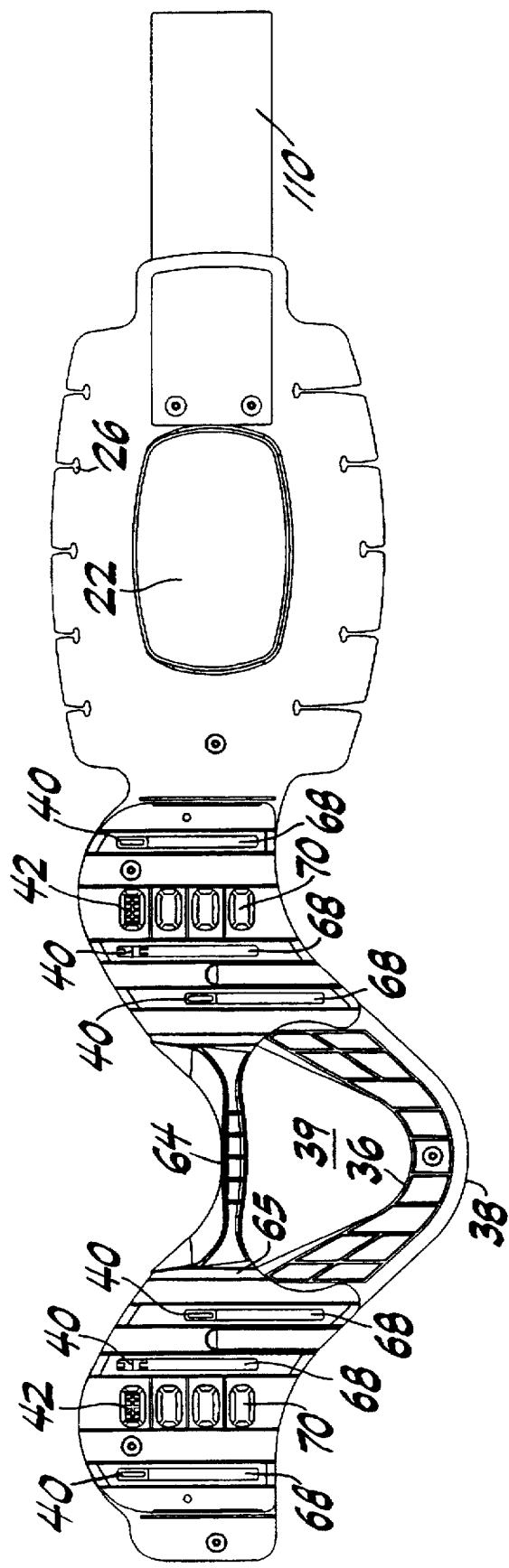
FIG. 3 is a plan view of the interior side of the collar shown in FIG. 1, minus the foam padding.
Figure 4A:
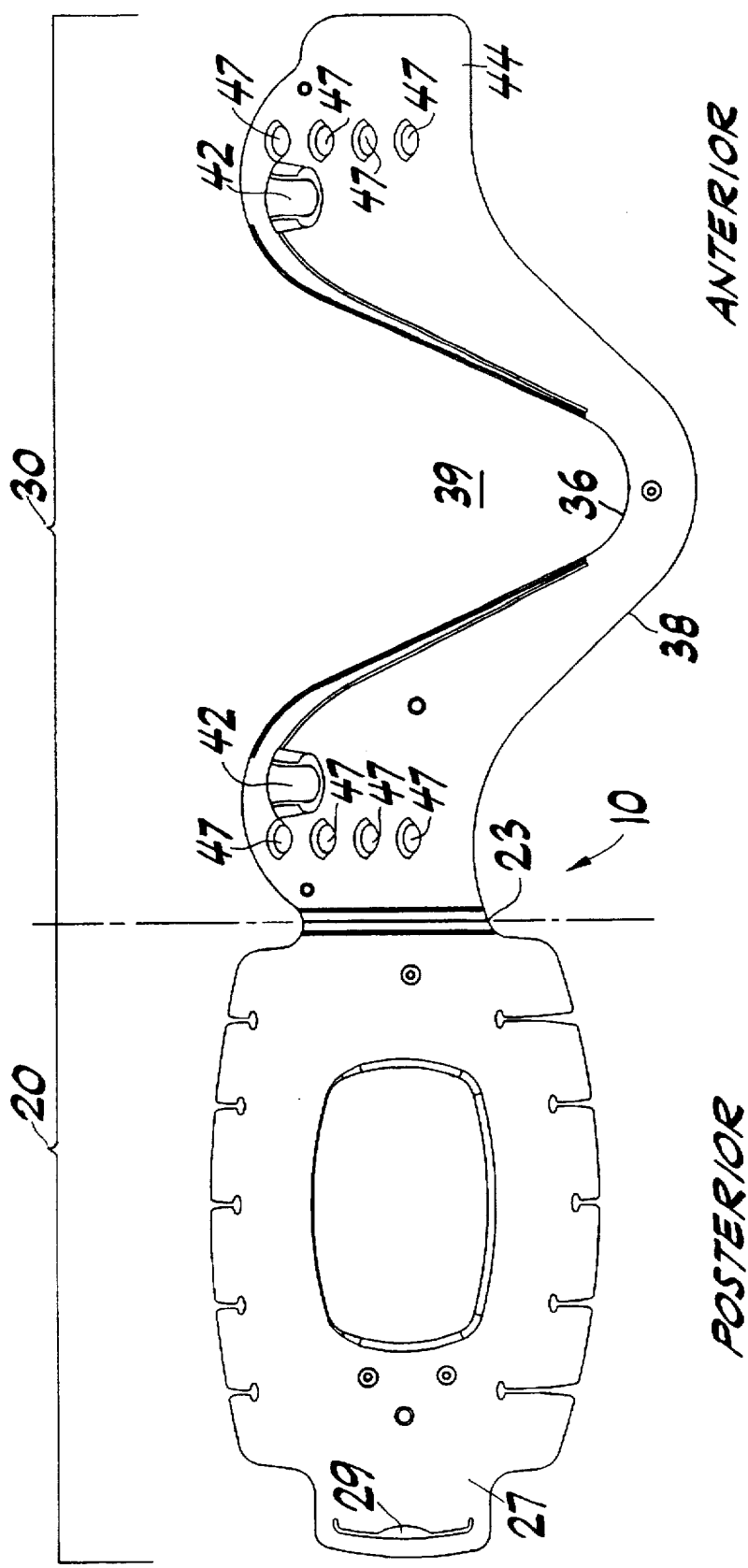
FIG. 4A is a plan view of the exterior side of the neck band employed in the collar.
Figure 4B:
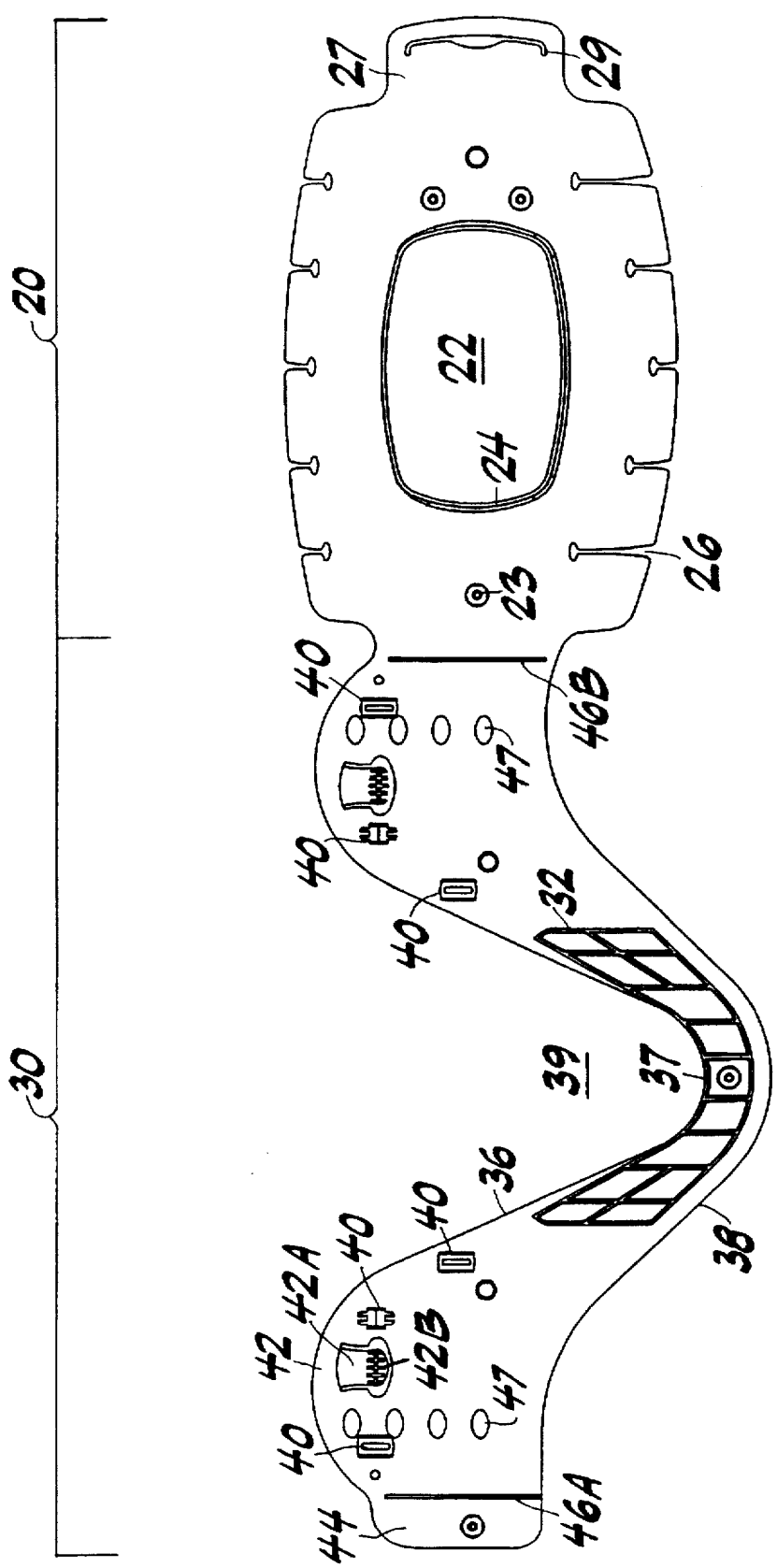
FIG. 4B is a plan view of the interior side of the neck band shown in FIG. 4A.

The neck band 10 of the collar serves as the platform to which the other components are directly or indirectly attached. Referring now to FIGS. 4A and 4B, neck band 10 is a molded, generally flat flexible plastic part having two subsidiary components, a back portion 20 and a front portion 30, the relational terms "front" and "back" describing where these halves of the neck band 10 are centered with respect to the wearer when the collar is in place. (Alternatively, this and the other elements of the collar may be extruded or die cut.) The back portion 20 comprises a generally flat portion having a series of serrations or slots 26 along its periphery that help provide a suitable level of conformability of the collar to the wearer, while still permitting the neck band to be made sufficiently stiff to provide support of the head to prevent extension. In the center of the back portion 20 is a spinal access hole 22 that provides access to the back of the wearer's neck and spine. The spinal access hole 22 is demarcated by an anteriorly directed (i.e., directed into the plane of the page of FIG. 4A) flange 24, which provides the back portion 20 with additional stiffness. At the lateral extremity of the back portion 20 is a tab portion 27 that has a slot 29 for receiving a strap 110 of the hook and loop type. As shown in FIG. 3, the strap 110 is attached to the back of the neck band via rivets or other conventional attachment mechanisms, such as adhesive, welds, etc.

As seen in FIGS. 4A and 4B, in this embodiment the back portion 20 and the front portion 30 are formed of the same piece of plastic joining together or merging at a side portion 23. (Alternatively, the front portion and the back portion could be formed as separate pieces and connected together either during the manufacturing process or in the field just prior to application of the collar to the wearer. The front portion 30 has a deeply curved configuration, having an upper edge 36 and a lower edge 38 that are in the general shape of cosine curves of varying amplitude but similar period. The upper edge 36 bottoms out at a trough 37, which divides the front portion 30 into two generally equal halves. Lower edge 38 conforms generally to the shape of the wearer's shoulders and clavicle. Medially and laterally arrayed about the bottom of edges 36 and 38 on the posterior side of the front portion 30 of the neck band 10 (the left-hand half of FIG. 4B) is a pattern of posteriorly-directed ribs 32 that provide stiffening. Laterally displaced from these ribs are ribs 46A and 46B that serve to space padding (described below) further away from the neck band 10 and so avoid snagging of the mandible support 60 on the padding.

On each side of the trough or tracheal opening 39 are three pairs of spaced apart male sliders 40, which protrude posteriorly from the interior side of the front portion 30. As shall be explained in further detail below, the sliders cooperate with female slider slots on the mandible support 60. A male locking member 42, which in the particular embodiment illustrated consists of a lock tab having a posteriorly directed protrusion 42b on the end of a tab 42A, is located on either side of the front portion 30 near the crests of the upper edge 36.

The free end of the front portion 30 terminates with a tab 44, to which is attached a pad 98 of hook-and-loop type fasteners (see FIG. 1). The pad 98 may be a separate part that is adhesively attached to the neck band, or it may be molded directly onto the surface of the neck band or a portion of the surface of the neck band may be roughened so as to provide a region of hook fasteners. In either case, it cooperates with the complementary hook-and-loop fasteners on the free end of the strap 96 to enable the cervical collar to be secured to the wearer. Typically, the strap 96 will bear loop-type fasteners and pad 98 will bear hook-type fasteners.

Figure 5A:
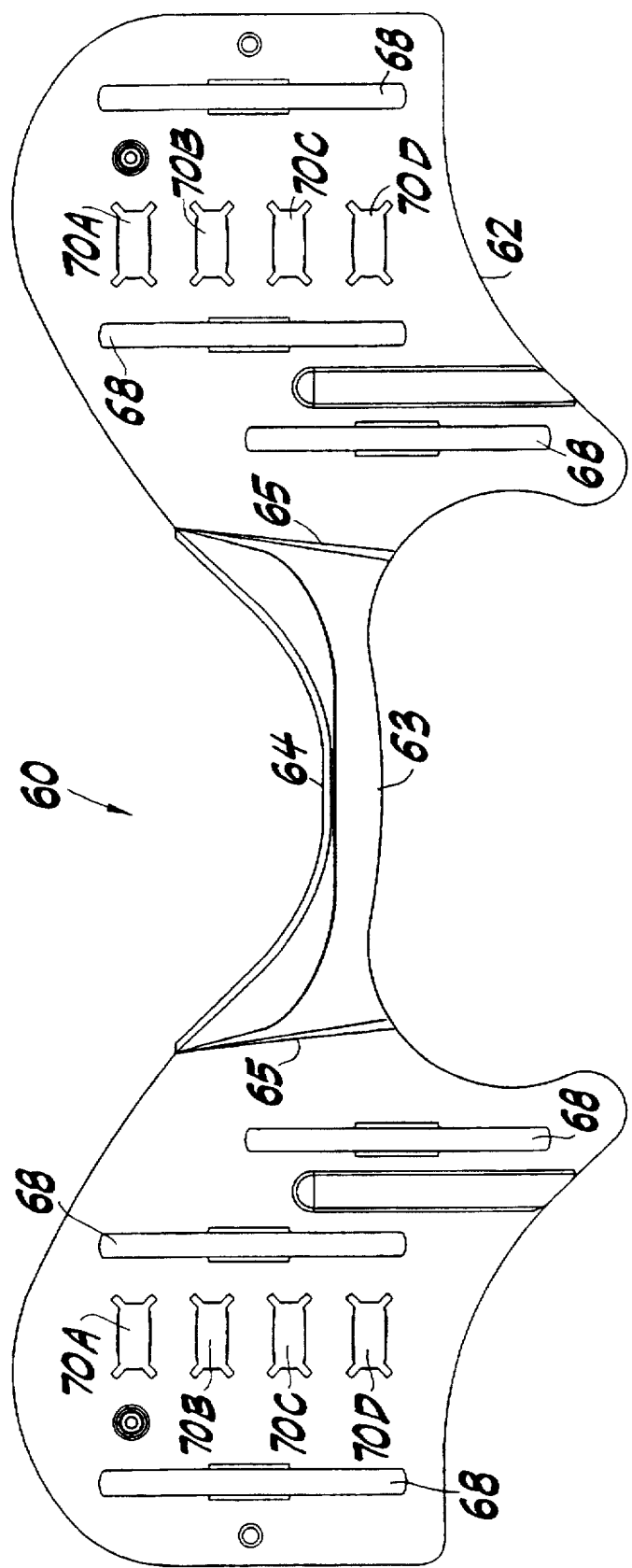
FIG. 5A is a plan view of the exterior side of the mandible support employed in the collar.
Figure 5B:
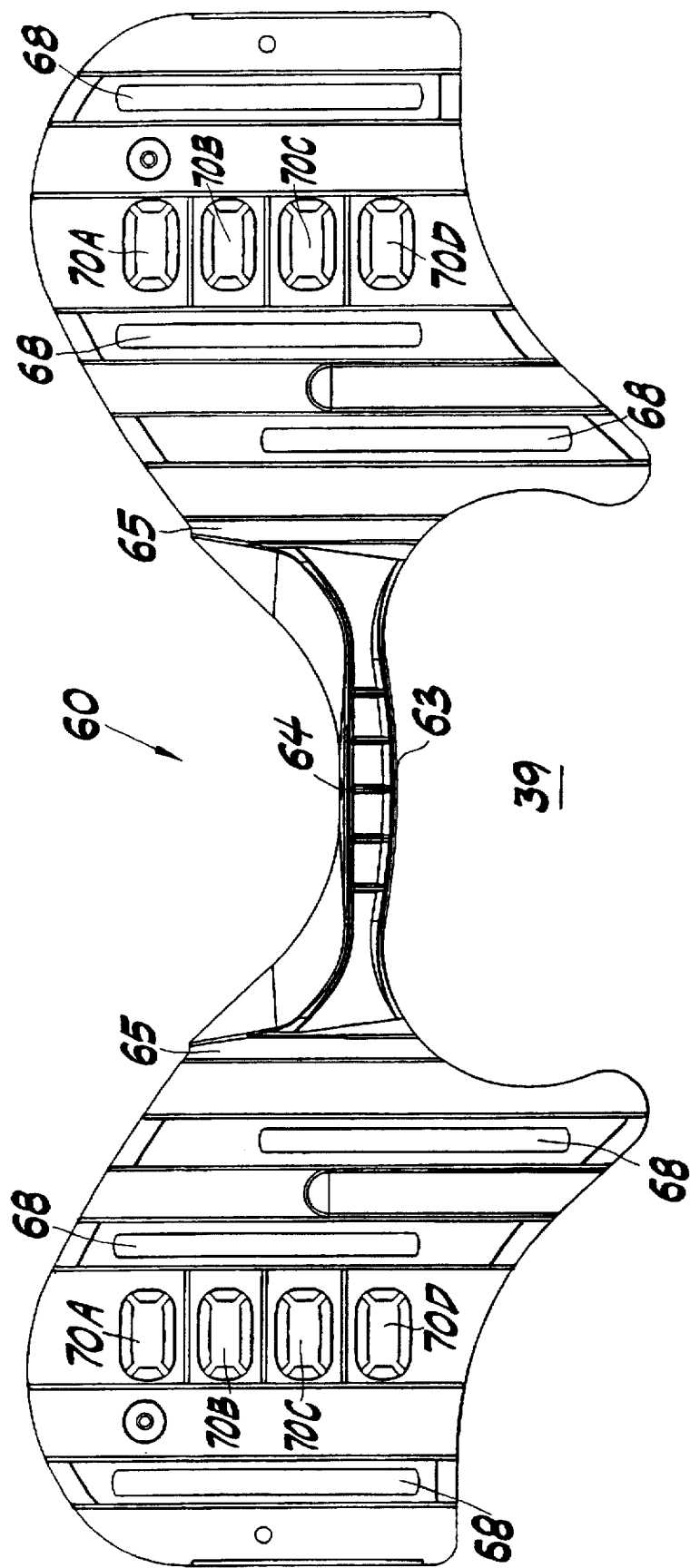
FIG. 5B is a plan view of the interior side of the mandible support shown in FIG. 5A.

The mandible support 60 (see FIGS. 5A and 5B) has an overall butterfly configuration with generally flat wing portions 62 symmetrically arranged about an anteriorly directed chin cup 64 extending out of the plane of the wing portions 62. (An alternative approach is to use the flat-folding mandible support arrangement set forth in Reissue U.S. Pat. No. 32,219 to Garth. The contents of this patent are incorporated herein by reference for this purpose). The chin cup 64 is bounded by a pair of score lines or bands of reduced thickness 65. These score lines, which are only half as thick as the surrounding material, permit the wings to hinge into place to form a continuous supporting surface when the collar is applied. (Otherwise, the chin cup 64 may be too rigid to permit bending of the wings with respect to the chin cup.)

The lower edge 63 of the mandible support 60, in cooperation with the upper edge 36 of the front portion 30 of the neck band 10, defines a tracheal access opening 39 that provides access to the throat of the wearer.

Each wing 62 has a series of three parallel slider slots 68 and a column of female locking holes 70. The slider slots 68 (which may be stiffened with ribbing of adjacent portions of the mandible support 60) are sized and configured to cooperate with the male sliders 40 on the front portion 30 on the neck band 10, so as to permit only shiftable translatory movement (corresponding to a vertical, or "height" positioning) between the two when the former are inserted into the latter. The relative position of the front portion of the neck band and the mandible support, and hence the vertical displacement between the two, is fixed by the insertion of the male locks 42 into the desired pair of female locking holes 70 (which also provides both audible and tactile feedback). In the embodiment shown, four pairs of locking holes 70 are provided. These correspond to the four most commonly used sizes of cervical collar (usually referred to as Tall, Regular, Short, and No-Neck).

The tab locking structure of the first illustrated embodiment is sufficiently robust to bear the loads encountered in use without vertical slippage of the mandible support 60 with respect to the neck band 10, an important consideration in a vertically properly fitted collar. This is partially due to the arrangement of having any loads from the wearer transferred to the neck band 10 via locking the neck band to each of the two wing portions 62, thereby dividing the load into two generally equal halves. A further advantage of this arrangement over relying on a centrally located connection to bear the brunt of the load is that it provides for an even degree of support at both the left hand and right hand extremities of the mandible support, which provides a correspondingly even and reliable degree of support to both the mandible and the mastoid process. This level of support is generally invariant across the range of vertical positioning. Consequently, a single collar constructed according to the principles of the invention can securely provide as many discrete vertical positions for height variability as there are pairs of locking holes 70, thereby obviating the need to stock additional sizes of collar.

Figure 7:
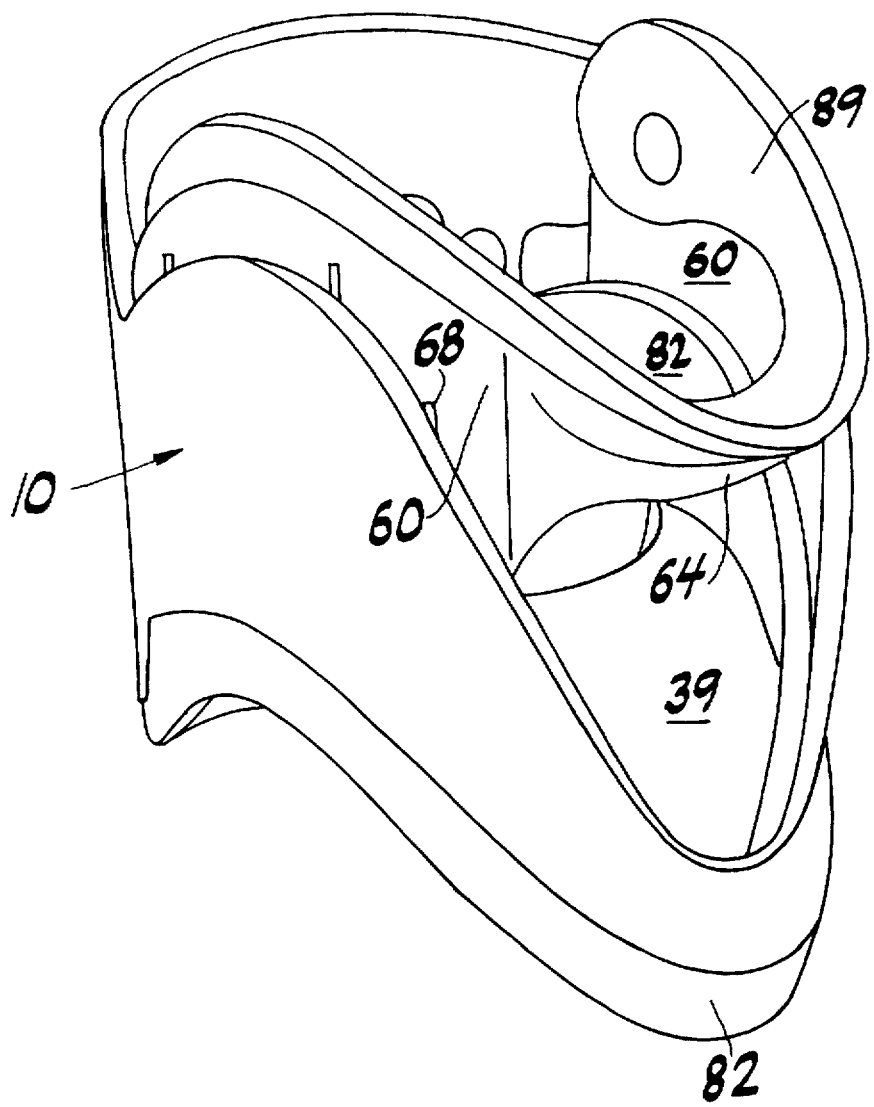
FIG. 7 is a perspective view of the collar in the configuration it assumes when wrapped about the neck of a wearer.

Another component of the cervical collar is padding 80, which is attached to the aforementioned components to enhance the comfort of the wearer (see FIGS. 1 and 7). The padding 80 consists of a piece of neck foam 82 and a second piece of chin foam 89. The neck foam 82 has the same general shape as the neck band 10 to which it is attached, but is sized to extend somewhat beyond the upper and lower margins of the neck band 10. The foam is attached by a plurality of snaps, rivets, or other attachment structure provided for this purpose, and may be permanently or replacably attached to the neck band and mandible support. In the illustrated embodiment, the neck band 10 is provided with a series of fastener holes for facilitating attachment of the neck pad via rivets (not shown). Similarly, chin foam 89 is configured to overlie and provide padding for the chin piece 30.

The neck band of the present invention can be made from various stiff flexible plastics, including without limitation high and low density polyethylene, polyvinylchloride, acrylonitrile-butadiene-styrene copolymer, polypropylene, etc. Padding, straps and strips can be joined to the collar by any suitable fastening means, including without limitation snap fasteners, staples and adhesive. Although hook and loop fastening material is used as the preferred means to hold the collar in its neck encircling conformation, other means can be used to perform the same function, such as straps, buckles, snaps, fasteners, cords, tabbed strips or any other substantially non-stretch material with latching means.

Additional refinements and structural variations are within the scope of the invention. For example, the back portion 20 of the neck band may be provided with pop-up tabs extending over the upper or lower edges of the neck band to selectively provide additional support to the head or back. The number of sliders and slots can be greater or fewer than shown, and their relative positions on the neck band and mandible support transposed. Indeed, the mandible support may be attached to either the front or back of the neck band. The number of discrete positions provided for by the collar may be increased or decreased, depending on the number of sizes to be provided.

With regard to the tab locking structure set forth above, alternative embodiments can employ other locking means, such as patches of hook and loop fasteners, snap fasteners (which can be provided either in addition to or in place of any other type of fastener and/or the slider and slot structure shown herein), etc.

Figure 8:
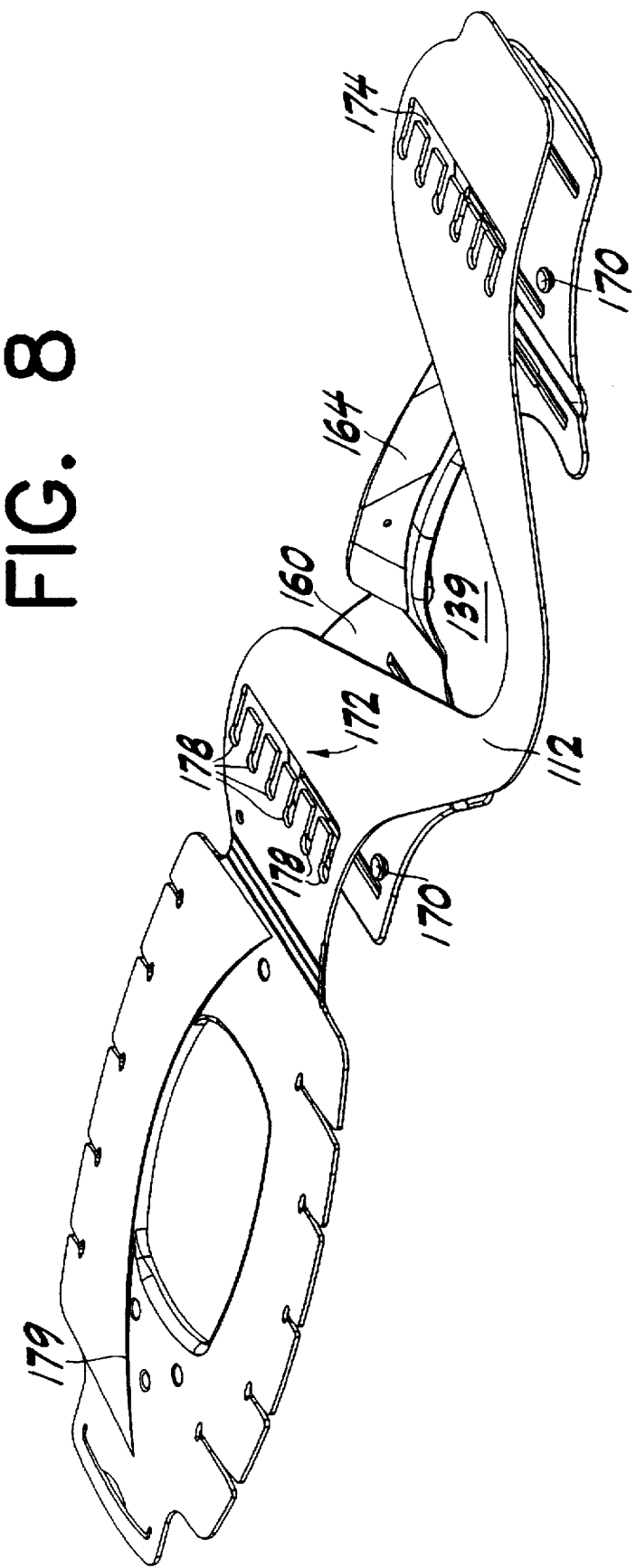
FIG. 8 is a perspective view of an alternative embodiment of a neck band and mandible support having a keyhole adjustment lock.

One such variant is shown in FIG. 8. The mandible support 160, which includes a chin cup 164, is connected to the neck band 112 via two posts 170 (located on opposite sides of the tracheal hole 139) and a notched track 172. The notched track is made up of a sliding track 174 extending from which are a series of notches 178 corresponding to locking positions. In the embodiment shown, the standard four adult sizes are provided for, along with two sizes for juveniles. To use, one would grasp the collar, sliding the mandible support with respect to the neck band to the desired position, and then laterally slide the two parts in order to engage the posts 170 into the notches 178.

This embodiment also illustrates the use of adjacent zones of material of varying thickness for greater visual contrast, here shown on the neck band as being demarcated along line 179. This further serves to draw attention to any indicia that may be placed in this area.

Figure 9:
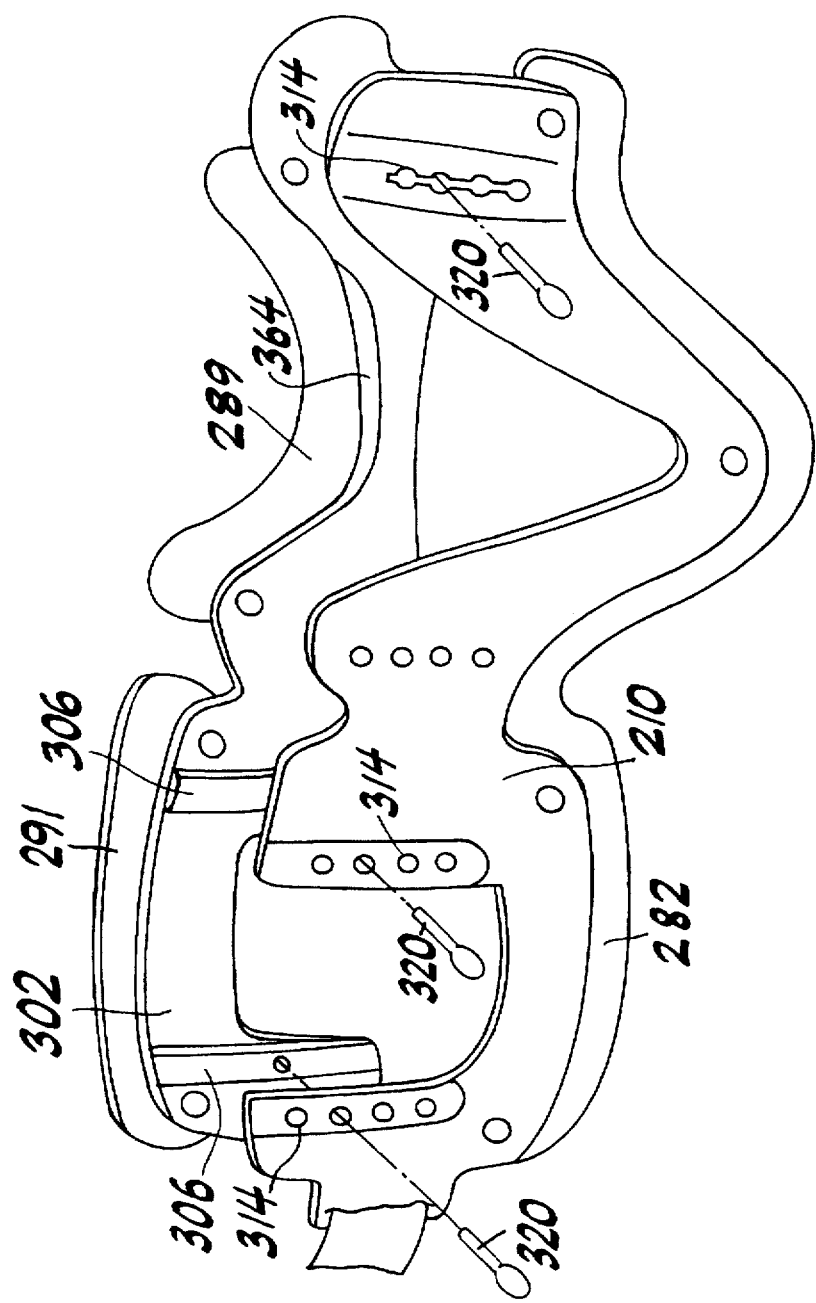
FIG. 9 is a frontal perspective, partially exploded view of a second embodiment of a collar constructed according to the principles of the invention.

FIG. 9 illustrates another embodiment of a collar constructed according to the principles of the invention, in which the mandible support extends generally the length of the neck band. The neck band 210 is provided with a series of holes 314 on both halves of the neck band. Connected to the neck band 210 is the mandible support 302 (which again has a built-in chin support cup 364), which is slidably connected to it at both the back and front portions of the neck band 210 via a plurality of tongue-and-groove slider elements 306 (the groove portion is on the facing side of the neck band 210 hidden from view). Padding 289, 291, and 282 is provided for comfort. Variations in sizing are made by sliding the mandible support 302 in its tongue-and-groove slots with respect to the neck band 210. Pins 320 are sized so as to securely link the neck band 210 with the mandible support 302 when forced through the corresponding hole when the desired position is reached (again corresponding to one of the discrete standard collar sizes provided for). Alternatively, other sizing selection structure such as is set forth herein may be employed instead.

Figure 6:
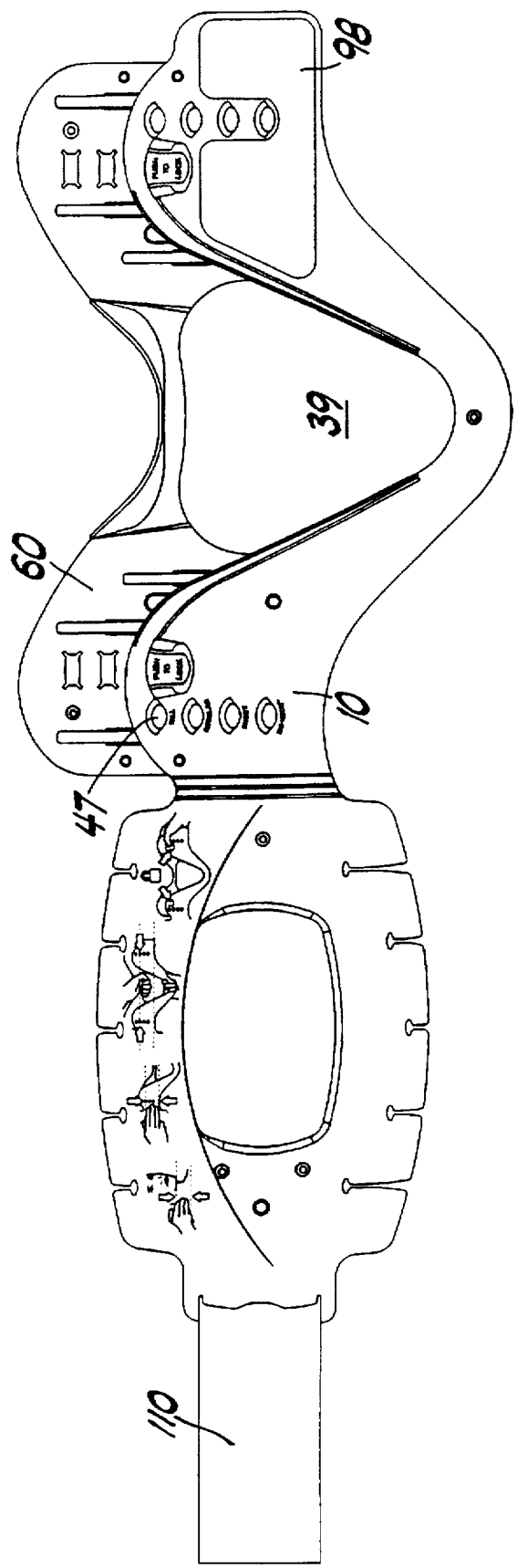
FIG. 6 is a plan view of an embodiment of a cervical collar similar to that shown in FIG. 3, in which the exterior of the neck band is provided with indicia illustrating how the collar is to be sized.

Use of the cervical collar of the invention will now be explained in reference to the embodiment shown in FIGS. 1–7 (essentially the same method can be practiced with the other embodiments). Instructions for affixing the cervical collar to the wearer may be provided on the surface of the collar in the form of graphical indicia, as shown in FIG. 6. Here, the posterior surface of the back portion 20 of the neck band 10 bears indicia illustrating how the collar is to be sized. The anterior surface of the front portion 30 is provided with a series of size windows 47 that are labeled with indicia of the corresponding size. The cervical collar is used as follows. First, the collar is sized to the wearer before being applied to the wearer:

1. With the wearer held in a neutral position, the technician uses his fingers to measure the distance from the top of the shoulders (the trapezius muscle) where the collar will sit, to the bottom of the chin (at the bony structure). This is the wearer's "key dimension."

2. Next, the technician uses his fingers to apply the key dimension to the collar. The fingers are aligned with the edge of the plastic neck band below the size windows (not the foam). The size window closest to the top finger is selected (tall, regular, short, or no-neck).

3. The mandible support 60 is positioned for the selected size (the size indicators on both sides of the trachea opening should be at the same setting).

4. Each side of the mandible support 60 is locked into place by pressing the two lock tabs 42. The tabs will snap into place and will be flush with the collar when locked.

After sizing, the collar is applied to the wearer in the following manner (depending upon his position):

1. The collar is held and then sharply flexed inward to preform the final shape of the collar and so ease its application.

2. With the wearer's head held in neutral alignment, the mandible support is positioned by sliding the collar up the chest wall of the wearer. Care should be taken that the chin is well supported. Any difficulty in positioning the mandible support may indicate the need to reposition or re-size the collar to the next smaller size. (If re-sizing is necessary, the collar should first be removed.)

3. The position of the wearer's head should be checked for proper alignment (neutral alignment should not be altered). The collar should be tightened by pulling the loop strap while supporting the collar by holding the edge of the trachea opening. The loop strap is then attached to the hook patch to secure the collar.

Once installed, constraining support is provided to both the mandible and the mastoid process behind the ear. This level of support prevents unwanted lateral bending and rotation, in addition to flexion and extension motions, for all of the selectable sizes of the collar.

What is claimed is:

1. A multiple position cervical collar comprising:
   a band formed of a stiff material including a front portion and a back portion:
   a mandible support formed of a stiff material, said mandible support having a central chin cup and a pair of wing portions, each wing portion located on one of the sides of the chin cup; and
   a connection between the mandible support and the band providing a series of selectable predefined positions between the two wing portions of said mandible support and the band, each predefined position defining a different distance between the center of the chin cup and a fixed point on the band, said connection comprising a projection located on one of said band and said mandible support that is movable from a first unengaged position to a second engaged position in cooperation with one of a plurality of openings on the other one of said band and said mandible support.

2. A cervical collar as set forth in claim 1, wherein the band is generally planar prior to use.

3. A cervical collar as set forth in claim 1, wherein the back portion of the band has a central opening for permitting access to the spine of the wearer of the cervical collar.

4. A cervical collar as set forth in claim 3, wherein the central opening is delimited from the band by at least one stiffening element.

5. A cervical collar as set forth in claim 1, wherein the periphery of the back portion of the band is serrated.

6. A cervical collar as set forth in claim 1, wherein the band further comprises:
   a strap, said strap being attached to the band near one end of the band; and
   attachment structure located on the opposite end of the band for cooperating with said strap to permit securement of the cervical collar to a wearer.

7. A cervical collar as set forth in claim 6, wherein the strap has a fastening surface having hook-and-loop fasteners, and the attachment structure on the opposite end of the band is of a cooperating hook-and-loop fastener.

8. A cervical collar as set forth in claim 7, wherein the attachment structure located on the band for cooperating with the strap is a patch of hook fasteners that is adhesively connected to the band, and the strap has a fastening surface of the loop type.

9. A cervical collar as set forth in claim 7, wherein a portion of the surface of the band is roughened so as to provide a region of hook fasteners for cooperation with strap.

10. A cervical collar as set forth in claim 7, wherein a portion of the surface of the band is shaped in the form of hook-and-loop fasteners.

11. A cervical collar as set forth in claim 7, further comprising a pad in the general shape of the band, and attachment means for connecting the pad to the band.

12. A cervical collar as set forth in claim 11, wherein the band has at least two ribs for spacing the pad from the band.

13. A cervical collar as set forth in claim 1, further comprising a pad having the general shape of the mandible support, said mandible support and said pad having attachment means for connecting the pad to the mandible support.

14. A cervical collar as set forth in claim 1, further comprising ribbing at selected portions of the band for stiffening the band.

15. A cervical collar as set forth in claim 1, wherein the band has indicia indicating the proper use of the cervical collar.

16. A cervical collar as set forth in claim 1, wherein the front portion of the band has an upper edge and a lower edge, said upper edge being steeply curved so as to define a trachea opening between the upper edge of the front of the band and the mandible support.

17. A cervical collar as set forth in claim 1, wherein the connection between the mandible support and the band transfers any load delivered to the mandible support to the band.

18. A cervical collar as set forth in claim 1, further comprising locking structure on the band and on the mandible support for locking the mandible support into one of a plurality of possible positions.

19. A cervical collar as set forth in claim 18, wherein the locking structure on the band comprises a pair of locking tabs located at spaced apart positions on the front portion of the band, and a plurality of male sliders protruding from the front portion of the band.

20. A cervical collar as set forth in claim 19, wherein the locking structure on the mandible support comprises a plurality of parallel slots located in the wings of the mandible support that are configured to mate with the male sliders on the band so as to permit sliding motion therebetween, and a plurality of female locking holes on the wings configured to cooperate with the locking tabs.

21. A cervical collar as set forth in claim 20, wherein the female locking holes are provided in two parallel columns, each pair of female locking holes defining a position of height selection.

22. A cervical collar as set forth in claim 21, wherein the number of female locking holes in each column is four.

23. A cervical collar as set forth in claim 20, wherein the mandible support is provided with ribbing.

24. A cervical collar as set forth in claim 1, wherein the chin cup is demarcated from the wings of the mandible support by a region along which the thickness of the mandible support is reduced.

25. A cervical collar as set forth in claim 1, wherein the band is sized to encircle the neck of a wearer.

26. A cervical collar as set forth in claim 1, wherein each predefined position corresponds to a standard collar size.

27. A cervical collar as set forth in claim 1, wherein the collar is made of plastic.

28. A cervical collar as set forth in claim 27, wherein the plastic is flexible.

29. A cervical collar comprising:
a band formed from a stiff material:
a mandible support formed from a stiff material, said mandible support having a central chin cup configured for receiving a chin and a pair of wing portions, each wing portion located on one of the sides of the chin cup, wherein the chin cup is demarcated from the wings of the mandible support by a region along which the thickness of the mandible support is reduced to a fraction of the thickness of the surrounding area;
a pad having the general shape of the mandible support, said mandible support and said pad having attachment means for connecting the pad to the mandible support; and
a direct connection between each of the two wing portions of the mandible support and the band, wherein the connection transfers the load delivered to the mandible support directly to the band.

30. A cervical collar comprising:
a first band formed from a stiff material;
a second band comprising a mandible support formed from a stiff material, said mandible support having a central chin cup and a pair of wing portions, each wing portion located on one of the sides of the chin cup;
a direct connection between each of the two wing portions of the mandible support and the first band, wherein the connection both transfers any load delivered to the mandible support directly to the first band and can be varied so as to alter the distance between the chin cup and a fixed point on the first band.

31. A cervical collar as set forth in claim 30, wherein one of the first and second bands comprises a strap having hook and loop fastener structure, said strap being attached to that band near one end of the band and the band further including cooperating hook-and-loop structure located on the opposite end of the band for cooperating with said strap to permit securement of the cervical collar to a wearer.

32. A cervical collar as set forth in claim 31, wherein the strap and cooperating hook-and-loop structure is located on the first band.

33. A cervical collar comprising:
a neck encircling band formed from a stiff flexible plastic material comprising a front portion and a back portion:
a mandible support formed from a stiff flexible plastic material, said mandible support having a central chin cup and a pair of wing portions, each wing portion located on one of the sides of the chin cup;
a connection between each of the two wing portions of the mandible support and the band, wherein the connection transfers any load delivered to the mandible support to the band and is adapted to provide a series of selectable positions between the two;
locking structure on the band and on the mandible support for locking the mandible support into one of a plurality of possible positions, said locking structure including a pair of locking tabs located at spaced apart positions on the front portion of the band, and a plurality of male sliders protruding from the front portion of the band, wherein the locking structure on the mandible support comprises a plurality of parallel slots located in the wings of the mandible support that are configured to mate with the male sliders on the band so as to permit sliding motion therebetween, and a plurality of female locking holes, provided in the form of two parallel columns, each pair of female locking holes defining a position of height adjustment, are located on the wings and are configured to cooperate with the locking tabs.

34. A multiple position cervical collar comprising:
a first band formed of a stiff material;
a second band comprising a mandible support formed of a stiff material, said mandible support having a central chin cup and a pair of wing portions, each wing portion located on one of the sides of the chin cup; and
a connection between the mandible support and the first band providing a series of selectable predefined positions between the two wing portions of said mandible support and the first band, each predefined position defining a unique distance between the center of the chin cup and the first band, said connection comprising a projection located on one of said bands that is movable from a first unengaged position to a second engaged position in cooperation with one of a plurality of openings on the other one of said bands.

35. A cervical collar as set forth in claim 34, wherein the first band has a front portion and a back portion, and the periphery of the back portion of the band is serrated.

36. A cervical collar as set forth in claim 35, wherein at least one of the bands has indicia indicating the proper use of the cervical collar.

37. A cervical collar as set forth in claim 35, wherein the connection between the mandible support and the first band transfers load delivered to the mandible support to the first band.

38. A cervical collar comprising:

a band formed from a stiff flexible plastic material;

a mandible support formed from a stiff flexible plastic material, said mandible support having a central chin cup and a pair of laterally extending portions, each laterally extending portion being located on one of the sides of the chin cup;

a connection between each of the two laterally extending portions of the mandible support and the band, wherein the connection transfers at least a portion of the load delivered to the mandible support to the band and is adapted to provide a series of selectable positions between the two, each of said positions defining its own distance between the center of the chin cup and the band; and locking structure on the band and on the mandible support for locking the mandible support into one of a plurality of possible positions, said locking structure including a pair of locking projections located at spaced apart positions on one of said band and said mandible support and a plurality of openings, provided in the form of two parallel columns defining pairs of openings located on the other of said band and said mandible support, each pair of openings defining a position of height adjustment, said openings being configured to cooperate with the locking projections.

39. A cervical collar comprising:

a band formed from a stiff flexible plastic material;

a mandible support formed from a stiff flexible plastic material, said mandible support having a central chin cup and a pair of laterally extending portions, each laterally extending portion being located on one of the sides of the chin cup;

a connection between each of the two laterally extending portions of the mandible support and the band, wherein the connection transfers at least a portion of the load delivered to the mandible support to the band and is adapted to provide a series of selectable positions between the two, each of said positions defining its own distance between the center of the chin cup and a fixed point on the band; and indicia disposed on the collar to indicate each of a plurality of sizes.

40. A multiple position extrication collar comprising:

a first band formed of a stiff plastic material;

a second band formed of a stiff plastic material;

one of said first and second bands being a neck encircling band formed to be fitted about at least a portion of a patient's neck;

one of said first and second bands including a chin support adapted to engage and support the chin of the patient;

a cooperative locking structure on said first and second bands for locking said bands into one of a plurality of positions, said locking structure including a pair of locking projections located at spaced apart positions on one of said bands and a plurality of cooperative openings, provided in the form of two parallel columns defining pairs of openings located on the other one of said bands, each pair of openings defining a position of height adjustment, said openings being configured to cooperate with the locking projections; and a closure disposed on one of said bands to facilitate encircling the collar about the neck of the patient.

* * * * *

UNITED STATES PATENT AND TRADEMARK OFFICE
CERTIFICATE OF CORRECTION

PATENT NO.   : 5,795,315　　　　　　　　　　　　　　　　Page 1 of 4
DATED        : August 18, 1998
INVENTOR(S)  : Traut et al It is certified that error appears in the above-identified patent and that said Letters Patent is hereby corrected as shown below:

On the title page, item [56] insert the following:

| | | |
|---|---|---|
| Re 32,219 | 8/1986 | Garth |
| 2,223,276 | 11/1940 | Ward |
| 2,692,595 | 10/1954 | Blair, Jr. |
| 2,735,424 | 2/1956 | Benjamin |
| 2,736,314 | 2/1956 | Hale |
| 2,801,630 | 8/1957 | Moore |
| 2,806,471 | 9/1957 | Breese |
| 2,807,260 | 9/1957 | Teufel |
| 2,818,063 | 12/1957 | Smith et al. |
| 2,820,455 | 1/1958 | Hall |
| 2,828,736 | 4/1958 | Monfardini |
| 2,911,970 | 11/1959 | Bartels |
| 3,024,784 | 3/1962 | Monfardini |
| 3,027,894 | 4/1962 | Moore |
| 3,042,026 | 7/1962 | Monfardini |
| 3,042,027 | 7/1962 | Monfardini |
| 3,060,930 | 10/1962 | Grassl |

UNITED STATES PATENT AND TRADEMARK OFFICE
CERTIFICATE OF CORRECTION

PATENT NO. : 5,795,315
DATED : August 18, 1998
INVENTOR(S) : Traut et al

It is certified that error appears in the above-identified patent and that said Letters Patent is hereby corrected as shown below:

| | | |
|---|---|---|
| 3,070,090 | 12/1962 | Taylor |
| 3,075,521 | 1/1963 | Grassl |
| 3,135,256 | 6/1964 | Gruber |
| 3,220,406 | 11/1965 | Connelly |
| 3,285,243 | 11/1966 | Yellin |
| 3,285,244 | 11/1966 | Cottrell |
| 3,530,853 | 9/1970 | Bond |
| 3,295,516 | 1/1967 | Grassl |
| 3,306,284 | 2/1967 | McKinley |
| 3,313,297 | 4/1967 | Applegate et al. |
| 3,320,950 | 5/1967 | McElvenny |
| 3,374,785 | 3/1968 | Gaylord, Jr. |
| 3,504,667 | 4/1970 | McFarlane |
| 3,507,273 | 4/1970 | Yellin |
| 3,512,523 | 5/1970 | Barnett |
| 3,696,810 | 10/1972 | Gaylord, Jr. |
| 3,724,452 | 4/1973 | Nitschke |

UNITED STATES PATENT AND TRADEMARK OFFICE
CERTIFICATE OF CORRECTION

PATENT NO. : 5,795,315  
DATED : August 18, 1998  
INVENTOR(S) : Traut et al

Page 3 of 4

It is certified that error appears in the above-identified patent and that said Letters Patent is hereby corrected as shown below:

| | | |
|---|---|---|
| 5,433,696 | 7/1995 | Osti |
| 5,437,612 | 8/1995 | Moore et al. |
| 5,520,619 | 5/1996 | Martin |
| 3,756,226 | 9/1973 | Calabrese et al. |
| 3,850,164 | 11/1974 | Hare |
| 3,916,884 | 11/1975 | Attenburrow |
| 3,916,885 | 11/1975 | Gaylord, Jr. |
| 3,921,626 | 11/1975 | Neel |
| 3,964,474 | 6/1976 | Fox |
| 4,041,940 | 8/1977 | Frankel et al. |
| 4,205,667 | 6/1980 | Gaylord, Jr. |
| 4,232,663 | 11/1980 | Newton |
| 4,325,363 | 4/1982 | Berkeley |
| 4,401,111 | 8/1983 | Blackstone |
| 4,413,619 | 11/1983 | Garth |
| 4,969,453 | 11/1990 | Heimann |
| 5,058,572 | 10/1991 | Schmid et al. |
| 5,097,824 | 3/1992 | Garth |

UNITED STATES PATENT AND TRADEMARK OFFICE
CERTIFICATE OF CORRECTION

PATENT NO. : 5,795,315

DATED : August 18, 1998

INVENTOR(S) : Traut et al

It is certified that error appears in the above-identified patent and that said Letters Patent is hereby corrected as shown below:

| | | |
|---|---|---|
| 5,215,517 | 6/1993 | Stevenson et al. |
| 5,230,698 | 7/1993 | Garth |
| 5,366,438 | 11/1994 | Martin, Sr. |

FOREIGN DOCUMENTS

| | | |
|---|---|---|
| WO 96/09802 | 4/1996 | International |
| 918,770 | | Germany |
| 1,199,921 | | Germany |
| 2,129,140 | 12/1972 | Germany |
| 2,507,887 | 12/1982 | France |

Signed and Sealed this

Eighth Day of February, 2000

Attest:

Q. TODD DICKINSON

*Attesting Officer*  *Commissioner of Patents and Trademarks*